United States Patent [19]

Takaishi et al.

[11] 4,309,448
[45] Jan. 5, 1982

[54] BRANCHED FATTY ACID CHOLESTEROL ESTER AND A COSMETIC COMPOSITION CONTAINING THE SAME

[75] Inventors: Naotake Takaishi; Kouichi Urata, both of Ichikai; Yoshiaki Inamoto, Utsunomiya; Kikuhiko Okamoto; Shuichi Tsuchiya, both of Ichikai, all of Japan

[73] Assignee: Kao Soap Co., Ltd., Tokyo, Japan

[21] Appl. No.: 191,825

[22] Filed: Sep. 29, 1980

[30] Foreign Application Priority Data

Oct. 31, 1979 [JP] Japan ................... 54-139788

[51] Int. Cl.³ .................... A01N 25/00; A61K 47/00
[52] U.S. Cl. ..................... 424/365; 260/397.2
[58] Field of Search ............. 424/238, 365, 59; 260/397.2

[56] References Cited

PUBLICATIONS

Chemical Abstracts, vol. 73, 1970 Pars. 107112x article by Hradec et al.

*Primary Examiner*—Elbert L. Roberts
*Attorney, Agent, or Firm*—Oblon, Fisher, Spivak, McClelland & Maier

[57] ABSTRACT

A branched fatty acid cholesterol ester represented by the formula (I):

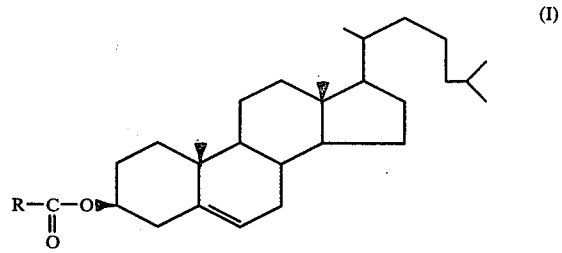

where, R is a saturated aliphatic hydrocarbon group having a total of 11 to 23 carbon atoms and including at least one alkyl substituent group attached on the main chain inbetween the carboxyl-bonding position and the center of the main chain; and cosmetic compositions containing the same are disclosed.

10 Claims, No Drawings

BRANCHED FATTY ACID CHOLESTEROL ESTER AND A COSMETIC COMPOSITION CONTAINING THE SAME

BACKGROUND OF THE INVENTION

1. Field of the Invention

The present invention relates to a novel fatty acid cholesterol ester and a cosmetic composition containing the same.

2. Description of the Prior Art

Cholesterol is widely distributed in nature, and especially in the animal body, it is distributed in almost all systems including brain cells and is believed to play a very important role in physiological processes. It is industrially used as a raw material for the synthesis of pharmaceuticals, as an additive for cosmetics and as a raw material for liquid crystals.

While it is clear that cholesterol is useful by itself, as mentioned above, there have been various attempts to reform cholesterol by subjecting it to various reactions to obtain its derivitives having novel properties which are not seen in cholesterol, per se.

Cholesterol has a unique sterol structure with a hydroxyl group at the $C_3$ position and an in-ring double bond at the $C_5$-$C_6$ position. It is conceivable that a chemical reaction suitable for an alcohol may be applied to the hydroxyl group at the $C_3$ position. For instance, various cholesterol esters obtainable by esterification of fatty acids and cholesterol, are known to be widely used, e.g., in the liquid crystal field (Japanese Patent Publication No. 11143 of 1970), as an intermediate for the synthesis of a steroid hormone (Japanese Patent Publication No. 40799 of 1972) and for a carcinostatic substance (Japanese laid-open patent application No. 25117 of 1974). Further, it is known that an addition product obtainable by the addition of an alkylene oxide such as ethylene oxide or propylene oxide to cholesterol, has an improved hydrophilic property over cholesterol by virtue of the addition of the alkylene oxide, and thus has an improved emulsion stability, and it is useful as a base material for a cosmetic and as an emulsifier (Japanese patent publication No. 28501 of 1975).

However, most of the above mentioned cholesterol derivatives have a high melting point and are normally solid at room temperature. Accordingly it is necessary to take special measures for their use, and in some cases, the amounts or the ranges of their use are limited. Some of them give irritation to the skin upon application and their use for cosmetics is accordingly limited.

A need therefore continues to exist for cholesterol based materials useful as emulsifiers which are liquid at room temperature and give little irritation to the skin.

SUMMARY OF THE INVENTION

Accordingly, one object of the invention is to provide a cholesterol based ester useful as an emulsion stabilizer which is liquid at room temperature and gives little irritation to the skin.

A further object of the invention is to provide a cosmetic composition utilizing a cholesterol based ester which is liquid at room temperature and gives little irritation to the skin.

Briefly, these objects and other objects of the invention as hereinafter will become more readily apparent can be attained by providing a branched fatty acid cholesterol ester represented by the formula (I)

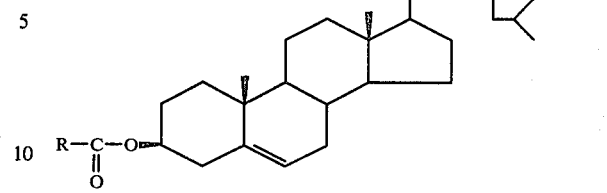

where, R is a saturated aliphatic hydrocarbon group having a total of 11 to 23 carbon atoms and including at least one alkyl substituent group attached on the main chain in between the carboxyl-bonding position and the center of the main chain.

DETAILED DESCRIPTION OF THE PREFERRED EMBODIMENTS

The branched fatty acid cholesterol ester of the present invention is represented by the formula (I):

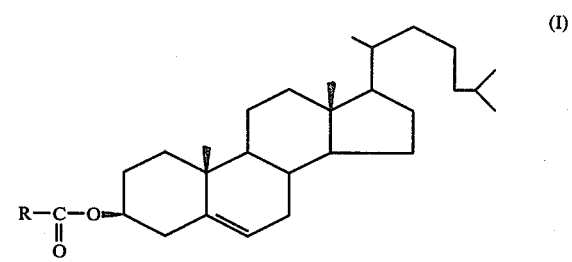

where, R is a saturated aliphatic hydrocarbon group having a total of 11 to 23 carbon atoms and including at least one alkyl substituent group attached on the main chain in between the carboxyl-bonding position and the center of the main chain.

The branched fatty acid (RCOOH) to be used for the preparation of the branched fatty acid cholesterol ester of the present invention, has 12 to 24 carbon atoms (i.e., 11 to 23 carbon atoms in R), but is preferably has 14 to 20 carbon atoms (i.e., 13 to 19 carbon atoms in R).

The branched fatty acid is a saturated branched chain fatty acid having at least one alkyl substituent group on its main chain at a position inbetween the bonding position of the carboxyl group and the center of the main chain. The material of this type is readily available from the materials of the petrochemical industry or from the materials of the oil and fat chemical industry.

As an example of such branched fatty acids obtainable from the material of the petrochemical industry, there is a branched fatty acid having a side chain at the α-position and represented by the following formula (II)

(where each $R_1$ and $R_2$ is a straight or branched chain saturated aliphatic hydrocarbon, and the total number of carbon atoms in $R_1$ and $R_2$ is 12 to 18).

The branched fatty acid having a side chain at the α-position and represented by the above formula (II) may be prepared, for instance, by subjecting a straight or branched chain aldehyde having 7 to 10 carbon atoms to an aldol condensation and then subjecting the α-branched unsaturated aldehyde thus obtained to hydrogenation and oxidation to obtain a branched saturated fatty acid. The most readily available branched saturated fatty acid prepared by this method, is 5,7,7-trimethyl-2-(1,3,3-trimethylbutyl)-octanoic acid, a branched fatty acid having 18 carbon atoms (e.g., sold by Nissan Chemical Industries Co., Ltd.) prepared by forming a branched aldehyde having 9 carbon atoms by an oxo synthesis of an isobutylene dimer, then subjecting the aldehyde to an aldol condensation, and subjecting the branched unsaturated aldehyde having 18 carbon atoms thus obtained to hydrogenation and oxidation.

The branched fatty acid having a side chain at the α-position and represented by the above formula (II) may also be prepared by forming a β-branched alcohol by a Guerbet reaction of a straight or branched chain primary alcohol having 7 to 10 carbon atoms, and then subjecting the β-branched alcohol to oxidation. The most readily available branched saturated fatty acid prepared by this method, is 2-heptyl undecanoic acid (e.g., sold by Mitsubishi Chemical Industries Ltd.) prepared by the Guerbet reaction of nonylalchol followed by an oxidation reaction.

The branched fatty acid having a side chain at the α-position and represented by the formula (II) may be prepared by either of the above mentioned methods or by any other method (e.g., a method which comprises forming an aldehyde having a side chain at the α-position by an oxo synthesis of an olefin having 13 to 19 carbon atoms and then oxidizing the aldehyde).

As preferred examples of the saturated branched fatty acid having a side chain at the α-position, there may be mentioned, in addition to the above mentioned 5,7,7-trimethyl-2-(1,3,3-trimethylbutyl)-octanoic acid, and 2-heptyl undecanoic acid, 2-hexyl decanoic acid, 2-octyldodecanoic acid and 2-pentyl nonanoic acid.

As an example of a saturated branched fatty acid obtainable from the materials of the oil and fat chemical industry, there is a fatty acid having a methyl branched chain represented by the following formula (III):

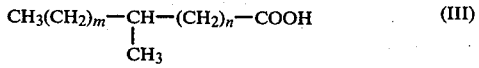

where, the total of m+n is 14 and the distribution is centered about m=n=7. Such a methyl branched chain fatty acid is obtainable, for instance, as a by-product in the preparation of a dimer of oleic acid (e.g., J. Amer. Oil Chem. Soc., 51,522 (1974)) and is referred to in this specification as "methyl branched isostearic acid". The methyl branched isostearic acid is sold, for instance, in the form of its isoprypyl ester (U.S. Emery Co., et ce).

The branched fatty acid cholesterol ester of the present invention is prepared from the above mentioned branched fatty acid or its derivative and cholesterol by the usual methods for the preparation of an ester. The fatty acid may be reacted directly with cholesterol for esterification, or either one of them may be converted to a reactive derivative and then esterified.

One of the reactive derivatives is a fatty acid halide. In a preferred embodiment, firstly a raw material branched fatty acid is converted to the corresponding acid halide by reacting 1 mole of the branched fatty acid with 1 to 5 moles, preferably 1 to 2 moles, of a halogenation agent such as thionyl chloride, thionyl bromide, phosgene, phosphorus trichloride, phosphorus pentachloride or phosphorus tribromide, at a temperature of 0° to 100° C., preferably 20° to 80° C. Then, the acid halide in an amount of 1 mole is reacted with 1 to 3 moles, preferably 1 to 1.5 mole, of cholesterol with use of 1 to 3 moles, preferably 1 to 1.5 mole, relative to the acid halide, of a dehydrohalogenation agent such as pyridine or quinoline in an inert solvent such as benzene, toluene, xylene or hexane (in an amount of 1 to 10 times, preferably 3 to 5 times, the volume of the acid halide), at a temperature of 50° to 100° C. preferably 60° to 80° C. while stirring and heating.

Upon the removal of an amine salt of hydrogen halide, the desired branched fatty acid cholesterol ester is obtained. The reaction is represented by the following formula:

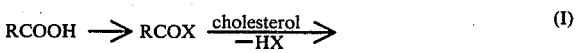

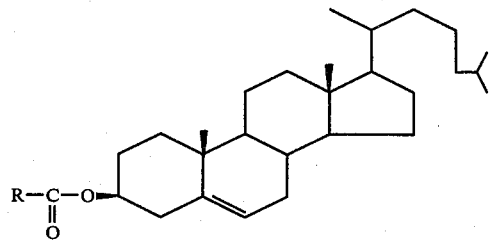

(where X is a halogen atom and R is as defined above).

The branched fatty acid cholesterol ester may be prepared by reacting a branched fatty acid directly with cholesterol without converting it to a reactive derivative. The direct reaction may be conducted in the presence or absence of an esterification catalyst. In the case where an esterification catalyst is used, it is preferred that free fatty acid and cholesterol are heated in the presence of an acid catalyst such as an inorganic acid e.g., hydrochloric acid, sulfuric acid or phosphoric acid, zinc chloride, tin chloride, zinc oxide or para-toluene sulfonic acid, in an inert solvent such as benzene, toluene, xylene or hexane, and the water formed is removed as an azeotrope out of the reaction system. In the case where no esterification catalyst is used, it is most preferred that the fatty acid and cholesterol are heated at a temperature of 200° to 230° C. and the water formed is removed under reduced pressure thereby obtaining the cholesterol ester, as disclosed in Japanese Patent Publication No. 11113 of 1976. In this case, it is preferable to add a small amount of a reducing agent to prevent the colour change of the product.

If a branched fatty acid ester such as a lower alkyl ester e.g., methyl ester, ethyl ester, or isopropyl ester, is readily available, it is possible to obtain a branched fatty acid cholesterol ester by the ester interchange reaction of the branched fatty acid ester and cholesterol with use of a usual ester interchange catalyst.

The branched fatty acid ester of the present invention thus obtained, is (1) liquid at room temperature, and (2) chemically stable as it is composed of a saturated hydrocarbon group, and (3) has an extremely low irritation to the skin. Accordingly, it is useful as an emulsion stabilizer for emulsions in general, especially as a component for an emulsion type cosmetic or a medicinal composition for application to the skin. If a component is in a solid state at room temperature, it is necessary to heat and melt it in actual use thus involving a cumbersome procedure, and if it is incorporated into an emulsion system, the viscosity of the emulsion decreases as time passes and eventually a separation of phases occurs.

The branched fatty acid cholesterol ester of the present invention is liquid at room temperature, and capable of stabilizing an emulsion together with an emulsifier. Further, as will be disclosed hereinafter, the branched fatty acid cholesterol of the present invention has an extremely low irritation to the skin, and accordingly it is possible to incorporate it in a product which is intended to be applied directly to the skin.

When the branched fatty acid cholesterol ester is used for a cosmetic composition, an effective amount thereof is added to a system comprising a cosmetic oil substance and water. It is preferred that the composition comprises 0.1 to 90%, preferably 1 to 50%, by weight of a cosmetic oil substance, 1 to 99%, preferably 20 to 90%, by weight of water 0.1 to 10% by weight of an emulsifier and 0.01 to 24%, preferably 0.03 to 4%, by weight of the branched fatty acid cholesterol ester. As the cosmetic oil substance, any known substance such as vaseline, liquid paraffin, natural fat and oil, a higher fatty acid alkyl ester, a higher aliphatic alcohol, or a higher fatty acid, may be used. Other materials which are normally incorporated in cosmetic compositions, may also be incorporated, and as such other materials, there may be mentioned a moisturizer, a thickening agent, an antiseptic agent, a medicinal component, a perfume, and an emulsion stabilizer.

Having generally described this invention, a further understanding can be obtained by reference to certain specific examples which are provided herein for purposes of illustration only and are not intended to be limiting unless otherwise specified.

PREPARATORY EXAMPLE 1

Into a reactor having a capacity of 2 liters and equipped with a thermometer, a reflux condenser, a dropping funnel and a stirrer means, 568 g (2.0 moles) of isostearic acid (i.e., 5,7,7-trimethyl-2-(1,3,3-trimethylbutyl) octanoic acid made by Nissan Chemical Industries Co., Ltd.) were charged. While stirring, 286 g (2.4 moles) of thionyl chloride were added dropwise from the dropping funnel under a nitrogen gas flow. As the dropwise addition of thionyl chloride proceeded, the reaction mixture underwent a colour change from colourless, light yellow to dark brown and at the same time gas generation was observed. During the dropwise addition of thionyl chloride, the temperature of the reaction mixture was maintained at room temperature. After the dropwise addition of thionyl chloride for about 3 hours, the reaction mixture was held at a temperature of 60° to 70° C. for about 3 hours in an oil bath. After ascertaining that there was no more generation of gas, low boiling point substances were removed under reduced pressure, and the remainder was subjected to a distillation under reduced pressure. 588 g of a distillate at 112° to 120° C./0.1 to 0.3 mmHg were obtained (97% yield). This was confirmed to be 5,7,7-trimethyl-2-(1,3,3-trimethylbutyl) octanoic chloride.

IR spectrum (liquid film):
2970, 2020, 2875, 1795 (C=O stretching vibration).
1480, 1390, 1370, 1260, 1210, 995, 930, 790, 710, 600 cm$^{-1}$ H$^1$-NMR spectrum (CCl$_4$ solvent): δ
0.9 (s, 24H, C$\underline{H}_3$—)
1.1 to 2.0

(m, 10H, —C$\underline{H}_2$— and —$\overset{|}{\underset{|}{C}}$—H)

2.5 (m, 1H, >C$\underline{H}$COCl)

PREPARATORY EXAMPLE 2

Into a reactor having a capacity of 2 liters and equipped with the same devices as employed in Preparatory Example 1, 571 g (2.0 moles) of isostearic acid (i.e., 2-heptyl undecanoic acid, made by Mitsubishi Chemical Industries Ltd.) were charged, and, while stirring, 286 g (2.4 moles) of thionyl chloride were dropwise added from the dropping funnel at room temperature under a nitrogen gas flow. As the dropwise addition of thionyl chloride proceeded, the reaction mixture underwent a colour change as was observed in Preparatory Example 1. During the dropwise addition of thionyl chloride, the temperature of the reaction mixture was maintained at room temperature. After the dropwise addition of thionyl chloride for about 3 hours, the reaction mixture was held at 60° to 70° C. for about 3 hours in an oil bath. After ascertaining that there was no more generation of gas, low boiling point substances were removed under reduced pressure and the remainder was subjected to a distillation under reduced pressure, whereupon 549 g of a distillate at 145° to 151° C./0.25 to 0.3 mmHg were obtained (91% yield). This was confirmed to be 2-heptyl undecanoic chloride.

IR spectrum (liquid film):
2960, 2925, 2850, 1790 (C=O stretching vibration)
1460, 1380, 900, 830, 720, 700, 600 cm$^{-1}$
H$^1$-NMR (CCl$_4$ solvent): δ
0.83 (t, 6H, C$\underline{H}_3$CH$_2$—)
1.0 to 2.0 (m, 28H, —C$\underline{H}_2$—)
2.65 (m, 1H, >C$\underline{H}$COCl)

PREPARATORY EXAMPLE 3

With use of a reactor having a capacity of 3 liters and equipped with the same devices as in Preparatory Example 1, 568 g (2.0 moles) of isostearic acid (Emery 875 isostearic acid made by U.S. Emery Co. and being a methyl branched fatty acid represented by formula (III)) was reacted with 520 g (4.4 moles) of thionyl chloride in the same manner as in Preparatory Example 1. After the reaction, low boiling point substances were removed under reduced pressure whereupon about 230 g of a low boiling point product which is considered to be thionyl chloride, were recovered. The remainder was subjected to a distillation under reduced pressure, whereupon 454 g of a distillate at 153° to 170° C./1.0 to 3.0 mmHg were obtained (75% yield). This distillate was confirmed to be methyl branched isostearic chloride.

IR spectrum (liquid film):
2950, 2920, 2850, 1800 (C=O stretching vibration),
1460, 1400, 1380, 950, 720, 680, 590 cm$^{-1}$ H$^1$—NMR spectrum (CCl$_4$): δ
0.6 to 1.0 (m, CH$_3$CH$_2$— and C$\underline{H}$—)
$\overset{|}{\underset{}{CH_3}}$
1.0 to 1.5 (m, —CH$_2$—)
1.5 to 2.0 (m, —CH—)
$\overset{|}{\underset{}{CH_3}}$ 2.77 (t, —CH₂COCl)

EXAMPLE 1

Into a reactor having a capacity of 3 liters and equipped with a thermometer, a dropping funnel, a reflux condenser, and a stirrer means, 281 g (0.73 mole) of cholesterol, 1100 ml of benzene and 65 g (0.82 mole) of pyridine were introduced in this order. While stirring, the reaction mixture was heated to 50° C. by an oil bath under a nitrogen gas flow condition, and then 212 g (0.70 mole) of 5,7,7-trimethyl-2-(1,3,3-trimethylbutyl) octanoic chloride obtained by Preparatory Example 1 were added dropwise from the dropping funnel over about 3 hours while maintaining the temperature of the reaction mixture at about 50° C. After the completion of the dropwise addition, the reaction mixture was further stirred for about 5 hours while heating it at a temperature of 60° to 80° C. The IR spectrum of the reaction product at this stage showed that there still remained a small amount of the acid chloride. White precipitates consisting of pyridine chloride in the reaction product were removed by filtration, and after removing the solvent under reduced pressure the filtrate thus obtained was heated under reduced pressure of 0.5 to 0.7 mm Hg at a temperature of 190° to 200° C. for about 5 hours. After this treatment, the IR spectrum showed that the acid chloride disappeared completely. The product thus obtained was vigorously mixed with benzene (1000 ml) and a diluted hydrochloric acid (1000 ml) and thereafter the benzene layer was separated. The benzene layer was dried with sodium sulfate anhydride and the benzene was removed under reduced pressure, whereupon 465 g of 5,7,7-trimethyl-2-(1,3,3-trimethyl-butyl) octanoic acid cholesterol ester were obtained as a viscous light yellow lipuid (96% yield).

IR spectrum (liquid film method):
2950, 2900, 2870, 1720 (C=O stretching vibration), 1470, 1380, 1360, 1240, 1220, 1160, 1030, 1010 cm⁻¹

H¹-NMR spectrum (CCL₄ solvent): δ
0.65 (s, 3H, steroid structure C-18 methyl group)
0.85 (d, 6H, steroid structure side chain C-26, C-27 methyl group)

---

0.87 (s, 24H, fatty acid side chain methyl group)
1.0 to 2.5 (m)

4.40 (m, 1H, —CO\O\— )

5.25 (m, 1H, steroid structure C-6 olefin proton)
Acid value           0.8 (Calculated value 0)
Saponification value 85.8 (Calculated value 86.0)
Hydroxyl value       0.7 (Calculated value 0)
Iodine value         41.0 (Calculated value 39.1)

---

EXAMPLE 2

Into a reactor having a capacity of 3 liters and equipped with the same devices as in Example 1, 271 g (0.70 mole) of cholesterol, 1500 ml of benzene, and 65 g (0.82 mole) of pyridine were introduced in this order. While stirring and supplying a nitrogen gas, 212 g (0.70 mole) of 2-heptyl undecanoic chloride obtained by Preparatory Example 2 were added dropwise from the dropping funnel. During this operation, the temperature of the reaction mixture was maintained at 25° to 30° C. After the completion of the dropwise addition of the acid chloride in about 2 hours, the reaction mixture was held at 60° to 80° C. for about 6 hours in an oil bath. The IR spectrum at this stage showed that there still remained a small amount of the acid chloride. The reaction mixture was treated in the same manner as in Example 1 and then subjected to a heat treatment in the same manner, whereupon the reaction mixture was confirmed to contain no acid chloride by means of the IR spectrum. 456 g of 2-heptyl undecanoic acid cholesterol ester were obtained as a light yellow liquid having a low viscosity (94% yield).

IR spectrum (liquid film):
2950, 2930, 2850, 1730 (C=O stretching vibration), 1465, 1380, 1365, 1260, 1160, 1050 cm⁻¹

H¹-NMR spectrum (CCl₄ solvent): δ
0.68 (s, 3H, steroid structure C-18 methyl group)
0.80 (d, 6H, steroid structure side chain C-26, C-27 methyl group)

---

1.00 (s, 3H, steroid structure C-19 methyl group)
0.8 to 1.1 (m, 6H, branched fatty acid side chain CH₃CH₂—)
1.1 to 2.4 (m)

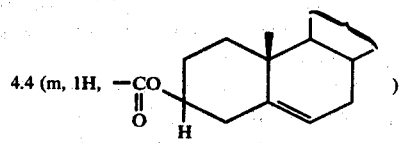

4.4 (m, 1H, —CO\O\— )

5.25 (m, 1H, steroid structure C-6 olefin proton)
Acid value           0.7 (Calculated value 0)
Saponification value 86.5 (Calculated value 86.0)
Hydroxyl value       0.5 (Calculated value 0)
Iodine value         40.0 (Calculated value 39.0)

---

EXAMPLE 3

Into a reactor having a capacity of 3 liters and equipped with the same devices as employed in Example 1, 281 g (0.73 mole) of cholesterol, 1500 ml of benzene and 100 g (1.27 mole) of pyridine were introduced in this order. While stirring, keeping the temperature at 25° to 30° C. and supplying a nitrogen gas, 212 g (0.70 mole) of the methyl branched isostearic chloride obtained by Preparatory Example 3 were added dropwise from the dropping funnel. After the completion of the dropwise addition, the reaction mixture was held at 50° C. for 3 hours and was further held at 70° to 80° C. for about 8 hours. By this treatment, the esterification reaction proceeded completely and it was confirmed by the IR spectrum that the reaction mixture contained no acid chloride. The reaction mixture was treated in the same manner as in Example 1 and 460 g of methyl branched isostearic acid cholesterol ester were obtained as a viscous, light yellow liquid (94% yield).

IR spectrum (liquid film)
2950, 2920, 2850, 1730 (C=O stretching vibration), 1460, 1370, 1160, 1000 cm⁻¹

H¹-NMR spectrum (CCl₄ solvent): δ
0.70 (s, 3H, steroid structure C-18 methyl group)
0.80 (d, 6H, steroid structure side chain C-26, C-27 methyl group)

---

1.00 (s, 3H, steroid structure C-19 methyl group)
0.80 to 1.0 (m, 6H, branched fatty acid CH₃CH₂— and -continued $-CH-$
$\ \ \ |$
$\ \ CH_3$ 1.0 to 2.0 (m)
2.2 (t, 2H, $-CH_2-CH_2-COO-$)

4.4 (m, 1H, $-CO-$ (steroid structure))
         $\ \ \ \|$
         $\ \ \ O$ 5.25 (m, 1H, steroid structure C-6 olefin proton)

| | |
|---|---|
| Acid value | 0.8 (Calculated value 0) |
| Saponification value | 84.8 (Calculated value 86.0) |
| Hydroxyl value | 0.7 (Calculated value 0) |
| Iodine value | 41.4 (Calculated value 39.0) |

As shown in Table 1, the branched fatty acid cholesterol esters of the present invention obtained by the above Examples, are liquids having a lower melting point than a straight chain fatty acid cholesterol ester and flowable at a room temperature.

TABLE 1

| | | Characteristic Values | Viscosities (cp) Temperature (°C.) |
|---|---|---|---|
| Present invention | 5,7,7-trimethyl-2-(1,3,3-trimethyl butyl) octanoic acid cholesterol ester (Product of Example 1) | Liquid | 42100/50<br>14000/60<br>6500/70 |
| | 2-Heptyl undecanoic acid cholesterol ester (Product of Example 2) | Liquid | 2720/30<br>740/50<br>440/60<br>200/70 |
| | Methyl branched isostearic acid cholesterol ester (Product of Example 3) | Melting point 25–30° C. | 5125/30<br>510/50<br>230/60<br>100/70 |
| Comparative products | Stearic acid cholesterol ester | Melting point 83° C. | |
| | Oleic acid cholesterol ester | 45° C. | |
| | Palmitic acid cholesterol ester | 90° C. | |
| | Lauric acid cholesterol ester | 91° C. | |

Test Example—Skin Irritation

The branched fatty acid cholesterol esters of the present invention obtained by the Examples were tested for irritation to the skin.

(A) Cumulative irritation on the skin of guinea pigs tested for 4 days (1) Test animal
Hartley type white female guinea pigs, having a weight of 350 to 400 g (2) Method for the test A side of the abdominal portion of the animal was hair cut by use of an electric hair cutter and shaved with an electric shaver thereby exposing the skin for application of a sample. Five animals were used, and a proper amount of the original substance to be tested was applied to the exposed portion in a shape of a disc having a diameter of about 2 cm. After the application, each animal was put in an individual cage, and after the applied sample was dried up, the animal was returned to a cage for breeding. This operation was repeated once a day for a total of four times.

The evaluation was made immediately before each application of the test substance and 24 hours after the final application on the basis of the following standards:

| (3) Evaluation standards | Evaluation Rating |
|---|---|
| − no reaction | 0 |
| ± slightly red spots | 1 |
| + clear red spots | 2 |
| + + clear red spots plus adema | 3 |
| + + + red spots, edema and scabbing, | |
| necrosis bulla | 4 |

(4) Test results of the repeated application of the test substances to the guinea pigs for four consecutive days

| Animal Nos | 24 hours after the first appln. | | | | | 24 hours after second appln. | | | | | 24 hours after third appln. | | | | | 24 hours after fourth appln. | | | | |
|---|---|---|---|---|---|---|---|---|---|---|---|---|---|---|---|---|---|---|---|---|
| | ① | ② | ③ | ④ | ⑤ | ① | ② | ③ | ④ | ⑤ | ① | ② | ③ | ④ | ⑤ | ① | ② | ③ | ④ | ⑤ |
| ① | − | − | − | − | ± | − | − | − | − | − | − | − | − | − | ± | − | − | − | − | ± |
| ② | − | − | − | − | − | − | − | − | − | − | − | − | − | − | − | − | − | − | − | ± |
| ③ | − | − | − | − | ± | − | − | − | − | − | − | − | − | ± | − | − | − | − | − | ± |
| ④ | − | − | − | − | ± | − | − | − | − | ± | − | − | − | − | ± | − | − | − | − | + |
| ⑤ | − | − | − | − | − | − | − | − | − | − | − | − | − | − | − | − | − | − | − | − |
| Average reaction strength | 0.0 | 0.0 | 0.0 | 0.0 | 0.6 | 0.0 | 0.0 | 0.0 | 0.0 | 0.2 | 0.0 | 0.0 | 0.0 | 0.0 | 0.6 | 0.0 | 0.0 | 0.0 | 0.0 | 1.0 |

1 5,7,7-trimethyl-2-(1,3,3-trimethylbutyl) octanoic acid cholesterol ester
2 2-heptyl-undecanoic acid cholesterol ester
3 Methyl branched isostearic acid cholesterol ester
4 Stearic acid cholesterol ester (Comparison purpose)
5 Oleic acid cholesterol ester (Comparison purpose)

(5) Conclusion

From the above results, it is seen that the oleic acid ester having a relatively low melting point among straight chain fatty acid cholesterol esters, produces irritation; while, the stearic acid ester which is not very useful because of its high melting point, produces no irritation. However, it is seen that the branched fatty acid cholesterol esters of the present invention which have practical use because of their low melting points, produce no irritation and, as such, they are very useful materials as an ingredient for a product for application to the skin.

[B] Sealed patch tests on human skin for 24 hours

A plaster was applied to a bending side of a front arm of each of 16 healthy men and 10 healthy women (i.e., a total of 26 persons). A proper amount of a test sample substance was applied to the lint cloth portion of a Torri patch test plaster (small size), and the plaster was placed on the skin for 24 hours. After the removal of the plaster, the evaluation was made 3 hours, 24 hours, and 48 hours later on the basis of the following standards:

—: no reaction
±: slightly red spots
+: clear red spots
++: clear red spots plus edema
+++: red spots, edema and scabbing, necrosis, bulla and papulae Results: Reactions of + or greater are regarded as positive, and the number of positive reactions relative to the total number of the persons tested are shown in the following ratios.

| Sample | 3 hours after removal of plaster | 24 hours after removal of plaster | 48 hours after removal of plaster |
|---|---|---|---|
| 1 | 0/26 | 0/25 | 0/26 |
| 2 | 0/26 | 0/25 | 0/26 |
| 3 | 1/26 | 1/25 | 0/26 |

1 5,7,7-trimethyl-2-(1,3,3-trimethylbutyl) octanoic acid cholesterol ester
2 2-heptyl-undecanoic acid cholesterol ester
3 methyl branched isostearic acid cholesterol ester

EXAMPLE 4

A W/O type skin cream was prepared which had the following composition:

| | |
|---|---|
| Methyl branched isostearic acid cholesterol ester | 1 (% by weight) |
| Lecithin | 0.5 |
| Vaselin | 15.0 |
| Hexadecyl-2-ethyl hexanoate | 10.0 |
| Ion exchanged water | Balance |

EXAMPLE 5

A W/O type milky lotion was prepared which had the following compositions:

| | |
|---|---|
| 2-heptyl undecanoic acid cholesterol ester | 0.2 (% by weight) |
| Liquid paraffin | 8.0 |
| Lecithin | 2.0 |
| Ion exchanged water | Balance |

Having now fully described this invention, it will be apparent to one of ordinary skill in the art that many changes and modifications can be made thereto without departing from the spirit or scope of the invention set forth herein.

What is claimed as new and desired to be secured by Letters Patent of the U.S. is:

1. A branched fatty acid cholesterol ester represented by the formula (I):

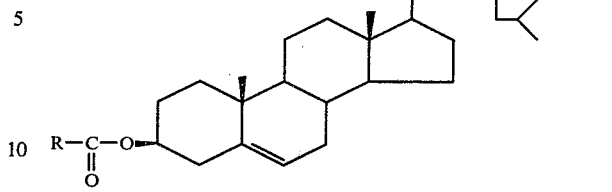

where R is a saturated aliphatic hydrocarbon group selected from the group consisting of:

(1) a radical represented by the formula (III):

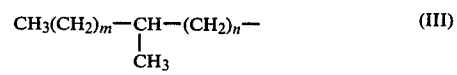

where the total of m+n is 14, and the distribution is centered about m=n=7; and (2) a radical selected from the group consisting of 5,7,7-trimethyl-2-(1,3,3-trimethylbutyl)-octyl; 2-heptylundecyl; 2-hexyldecyl; 2-octyldodecyl and 2-pentylnonyl.

2. The branched fatty acid cholesterol ester as claimed in claim 1, wherein R in the formula (I) is a hydrocarbon group represented by the formula (III):

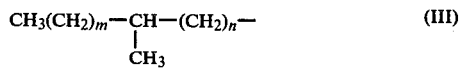

where the total of m+n is 14, and the distribution is centered about m=n=7.

3. The branched fatty acid cholesterol ester as claimed in claim 1, wherein R is a 5,7,7-trimethyl-2-(1,3,3-trimethylbutyl)-octyl group.

4. The branched fatty acid cholesterol ester as claimed in claim 1, wherein R is a 2-heptyl undecyl group.

5. A cosmetic composition comprising:
a cosmetic oil; water; an emulsifier; and a branched fatty acid cholesterol ester represented by the formula (I):

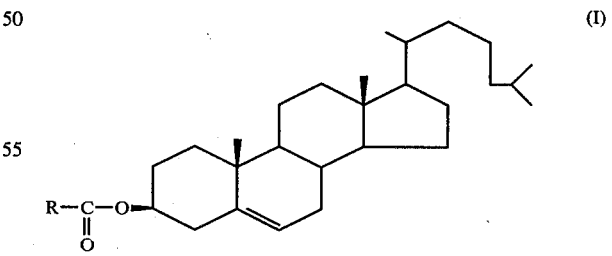

where, R is a saturated aliphatic hydrocarbon group having a total of 11 to 23 carbon atoms and including at least one alkyl substituent group attached on the main chain inbetween the carboxyl-bonding position and the center of the main chain.

6. The cosmetic composition as claimed in claim 5, wherein R in the formula (I) is a hydrocarbon group having a total of 13 to 19 carbon atoms.

7. The cosmetic composition as claimed in claim 6, wherein R in the formula (I) is a hydrocarbon group represented by the formula (III):

$$CH_3(CH_2)_m-\underset{\underset{CH_3}{|}}{CH}-(CH_2)_n- \quad (III)$$

where the total of m+n is 14, and the distribution is centered about m=n=7.

8. The cosmetic composition as claimed in claim 6, wherein R in the formula (I) is a hydrocarbon group represented by the formula (II):

$$\underset{\underset{R_2}{|}}{R_1-CH-} \quad (II)$$

where each of $R_1$ and $R_2$ is a straight or branched saturated aliphatic hydrocarbon group, and the total number of carbon atoms in $R_1$ and $R_2$ is 12 to 18.

9. The cosmetic composition as claimed in claim 5, wherein the cosmetic oil is present in an amount of 0.1 to 90 weight %, water is present in an amount of 1 to 99 weight %, and the branched fatty acid cholesterol ester is present in an amount of 0.01 to 24 weight %.

10. The cosmetic composition as claimed in claim 9, wherein the cosmetic oil is present in an amount of 1 to 50 weight %, water is present in an amount of 20 to 90 weight %, and the branched fatty acid cholesterol ester is present in an amount of 0.03 to 4 weight %.

* * * * *